United States Patent [19]

Simon et al.

[11] Patent Number: 5,746,222
[45] Date of Patent: May 5, 1998

[54] URINARY CONTINENCE DEVICE FOR MEN AND METHOD OF CONTROLLING URINARY INCONTINENCE BY USING SAME

[75] Inventors: John G. Simon, Boston; Carl J. Wisnosky, Spencer; Jeffrey C. Cerier, Franklin; Christopher C. Coulter, Newton Upper Falls; David E. Coats, Newton, all of Mass.

[73] Assignee: UroMed Corporation, Needham, Mass.

[21] Appl. No.: 572,332

[22] Filed: Dec. 14, 1995

[51] Int. Cl.$^6$ ............................................. A61F 5/48
[52] U.S. Cl. ........................... 128/885; 128/DIG. 25; 600/29
[58] Field of Search ............................ 128/846, 885, 128/DIG. 25, 842, 844; 600/29–31, 38–40; 604/349–356

[56] References Cited

U.S. PATENT DOCUMENTS

| | | | |
|---|---|---|---|
| 3,340,876 | 9/1967 | Hill | 128/295 |
| 3,512,185 | 5/1970 | Ellis | 4/110 |
| 3,528,422 | 9/1970 | Hodas | 128/290 |
| 3,661,155 | 5/1972 | Lindan | 128/295 |
| 3,726,277 | 4/1973 | Hirschman | 128/285 |
| 3,857,394 | 12/1974 | Alemany | 128/260 |
| 3,983,873 | 10/1976 | Hirschman | 128/285 |
| 4,046,147 | 9/1977 | Berg | 128/290 |
| 4,197,849 | 4/1980 | Bostick | 128/295 |
| 4,198,979 | 4/1980 | Cooney et al. | 128/295 |
| 4,209,009 | 6/1980 | Hennig | 128/1 |
| 4,258,704 | 3/1981 | Hill | 128/1 R |
| 4,261,340 | 4/1981 | Baumel et al. | 128/1 R |
| 4,421,511 | 12/1983 | Steer et al. | 604/329 |
| 4,457,314 | 7/1984 | Knowles | 128/760 |
| 4,484,917 | 11/1984 | Blackmon | 604/327 |
| 4,496,355 | 1/1985 | Hall et al. | 604/327 |
| 4,563,183 | 1/1986 | Barrodale et al. | 604/329 |
| 4,578,065 | 3/1986 | Habib | 604/336 |
| 4,593,053 | 6/1986 | Jevne et al. | 523/111 |
| 4,595,392 | 6/1986 | Johnson et al. | 604/385 |
| 4,627,848 | 12/1986 | Lassen et al. | 604/370 |
| 4,631,062 | 12/1986 | Lassen et al. | 604/385 |
| 4,638,790 | 1/1987 | Conway | 128/844 |
| 4,673,403 | 6/1987 | Lassen et al. | 604/385 |
| 4,690,677 | 9/1987 | Erb | 604/329 |
| 4,790,835 | 12/1988 | Elias | 604/349 |
| 4,795,449 | 1/1989 | Schneider et al. | 604/329 |
| 4,804,380 | 2/1989 | Lassen et al. | 604/385 |
| 4,821,742 | 4/1989 | Phelps | 128/844 |
| 4,822,347 | 4/1989 | MacDougall | 604/329 |
| 4,846,819 | 7/1989 | Welch | 604/329 |
| 4,846,824 | 7/1989 | Lassen et al. | 604/385 |
| 4,846,909 | 7/1989 | Klug et al. | 156/232 |
| 4,863,448 | 9/1989 | Berg | 604/349 |
| 4,979,947 | 12/1990 | Berman | 604/369 |

(List continued on next page.)

FOREIGN PATENT DOCUMENTS

| | | | |
|---|---|---|---|
| 0407218 | 9/1991 | European Pat. Off. | |
| 754481 | 8/1956 | United Kingdom | 81/2 |
| 9004431 | 5/1990 | WIPO | |

OTHER PUBLICATIONS

"Male Assistant" by Insight Medical Publication date: unknown.

*Primary Examiner*—Michael A. Brown
*Attorney, Agent, or Firm*—Lorusso & Loud

[57] ABSTRACT

A urinary continence device for males, having a body to cover and seal the urethra of the wearer and capable of conformably securing to the penis of the wearer. In the preferred embodiment, the body has a substantially hemispherical configuration and is sized to cover the glans penis. One or more adhesives may be used to adhere the device to the penis and the one or more adhesives may be in a continuous or discontinuous layer. The device may additionally include a locating member to assist in placement and may provide additional sealing properties. In use, the body seals the urethra so as to prevent urine leakage. To void, the wearer simply removes the device, and reapplies the device or a new device when evacuation is complete.

13 Claims, 6 Drawing Sheets

U.S. PATENT DOCUMENTS

| | | | |
|---|---|---|---|
| 4,981,465 | 1/1991 | Ballan et al. | 600/32 |
| 4,990,338 | 2/1991 | Blank et al. | 424/443 |
| 5,057,096 | 10/1991 | Faglione | 604/385.1 |
| 5,071,433 | 12/1991 | Naestoft et al. | 623/7 |
| 5,074,855 | 12/1991 | Rosenbluth et al. | 604/335 |
| 5,114,380 | 5/1992 | Larsen | 452/176 |
| 5,114,419 | 5/1992 | Daniel et al. | 604/385 |
| 5,131,906 | 7/1992 | Chen | 600/29 |
| 5,160,341 | 11/1992 | Brenneman et al. | 606/198 |
| 5,234,409 | 8/1993 | Goldberg et al. | 604/96 |
| 5,263,947 | 11/1993 | Kay | 604/349 |
| 5,334,175 | 8/1994 | Conway et al. | 604/352 |
| 5,336,208 | 8/1994 | Rosenbluth et al. | 604/329 |
| 5,421,350 | 6/1995 | Friedman | 128/844 |

URINARY CONTINENCE DEVICE FOR MEN AND METHOD OF CONTROLLING URINARY INCONTINENCE BY USING SAME

CROSS REFERENCE TO RELATED APPLICATION

This application is related to U.S. application Ser. No. 08/124,264, filed Sep. 20, 1993, entitled "Urethral Plug having Adhesive for Enhanced Sealing Capabilities and Method of Using Said Plug."

FIELD OF THE INVENTION

This invention relates to the control of urinary incontinence and is directed more particularly to a urinary continence device for men, and a methodology for controlling incontinence in men by using such a device.

BACKGROUND OF THE INVENTION

Urinary stress incontinence is the involuntary loss of urine when the pressure within the urethra exceeds the maximum urethral pressure required for maintaining closure or continence. Maximum urethral pressure is exceeded during physical stress, or increased abdominal pressure, from activities such as sneezing, laughing, or lifting.

There are in existence many methods used to address the problem of incontinence, including surgical corrective techniques, surgically implanted indwelling devices, physician prescribed and inserted indwelling devices, bulking injections, as well as externally worn devices that collect or absorb urine. Each method has its drawbacks.

Surgically implanted devices may not be appropriate for patients with mild incontinence, or for those with other medical conditions that place them at risk for surgery. Additionally, one must consider the prohibitive cost of surgery. There are also the problems of encrustation, irritation, infection, toxic reactions to materials and tissue necrosis with surgically implanted devices. Moreover, surgically implanted devices traditionally have a low long term success rate.

Indwelling devices that are inserted by a physician, without involving surgical implantation, are also known. These devices are inserted by a physician through the urethral orifice and allow the wearer to void either past or through the device. These devices have generally been very complicated, difficult to manufacture and therefore expensive. In practice, such devices have proven difficult to use for the wearer as they are uncomfortable and can be cumbersome to manipulate to void. Additionally, these devices, because they are indwelling, may cause some of the numerous complications associated with surgically implanted devices, such as encrustation, irritation and infection.

Bulking injections have been used, especially to treat those with less severe incontinence. These injections are performed at the sphincter site, and involve the use of autologous fat, collagen, TEFLON, a trademark of E. I. Du Pont de Nemours of Wilmington, Del. for tetrafluoroethylene fluorocarbon polymers, hyaluronic acid or other polymers, to augment urethral coaption without fibrosis and scarring. While the procedure is relatively simple to perform and involves minimal discomfort and lost time to the patient, the site of the injection is often fibrotic as a result of radiation and/or surgery such as a prostatectomy, and therefore the tissue is less likely to expand. There are also the risks of migration of the bulking agent, infection at the tissue site, retention and some patients have complained of a burning sensation at the site. Additionally, the procedure has a relatively low success rate for men as compared to women.

External devices include those which use catheters and clamps. For a male, a clamping device is disposed about the penis so actuation of the device compresses the urethra, thereby preventing the unintentional discharge of urine. These devices are uncomfortable for the users and they can make the voiding process complicated and cumbersome (e.g., clamping device has to be removed and re-secured for each voiding). For clamping devices, there is also the potential for tissue necrosis in the clamp area.

The devices using a catheter involve collecting discharges from the urethra (e.g., using a condom type of mechanism about the penis) and transporting the collected urine to a storage bag or device. The catheter devices, because they involve collecting urine external to the body, create the potential for undesirable odors and spillage as well as requiring the collected urine to be separately discharged. There is also the potential for irritation and maceration of tissue when using the catheter devices such as the condom catheter.

There are also certain external devices that do not require insertion into the urethra, such as absorbent pads, diapers and the like. A urine absorbing pad is described in U.S. Pat. No. 4,863,448. These pads may include a liquid absorbing layer or a gel like material to absorb urine discharges. Such pads are bulky, susceptible to migration, often lack effectiveness in preventing leakage and provide no effective protection against undesirable odor. Moreover, these devices are expensive to use over time and are often associated with skin problems in the wearer.

Ideally, the problem of urinary incontinence in men is addressed with a device that is discrete, comfortable, simple to use and manipulable by the wearer.

SUMMARY OF THE INVENTION

It is, therefore, an object of the present invention to provide a urinary continence device that successfully treats the problems associated with urinary stress incontinence.

Another object of the present invention is to provide a urinary continence device for men that has no significant risk of complications associated with known devices as described above.

Another object of the present invention is to provide a urinary continence device that is discrete and can be worn in comfort.

A further object of the present invention is to provide a urinary continence device that can be manipulated easily by the wearer for application and to allow for voiding.

Another object of the present invention is to provide a urinary continence device for which long term use is not prohibitively expensive.

It is another object of the present invention to provide a urinary continence device that does not restrict blood flow to the penis.

Still another object of the present invention is to provide a method for using a urinary continence device to control urinary incontinence.

A urinary continence device for males is provided comprising a body that conformably secures to the penis and covers and seals the urethra of the wearer. In the preferred embodiment, the body has a hemispherical structure and is sized to cover the glans penis. The device may additionally include at least one adhesive to anchor the device to the penis of the wearer, and if so, the at least one adhesive is preferably positioned on the inner surface of the body so as to adhere the body to the penis and the adhesive may be in a continuous or discontinuous layer. After voiding, the wearer may reapply the device or apply a fresh device.

These and other objects of the present invention will be apparent from a review of the detailed description of the preferred embodiments, taken together with the drawings, in which like reference numbers refer to like members in the various views.

DETAILED DESCRIPTION OF THE PREFERRED EMBODIMENTS

The present invention is a novel urinary continence device for men comprising a body that conformably secures to the penis and seals at the urethra or just outside the urethra. Preferably, the body is sized to cover the glans penis of the wearer. A substantially hemispherical structure is the preferred shape for the body. One or more adhesives may be applied on the body to adhere the body in place. When the device is in place, the body seals the urethra, thereby preventing the involuntary loss of liquid, especially urine from the bladder. The device is removed to allow for evacuation of the bladder, and the device may be reusable, so that after evacuation, the device is reapplied. Alternatively, a fresh device may be used after voiding.

The device of the present invention is particularly suitable for men suffering from urinary stress incontinence, and provides a comfortable, discrete, and relatively inexpensive means to manage urinary incontinence. The device is also suitable for those with dribble incontinence, in which a small amount of urine or semen may remain temporarily in the urethra after urination or ejaculation, respectively, and drip out of the urethra some time later. The device of the present invention will be useful for both the circumcised and uncircumcised penis.

The device of the present invention can be made of a soft, flexible biocompatible material such as polyurethane, polyethylene, polypropylene, latex, silicone, foamed urethane, DYNAFLEX (a trademark of GLS Corporation of Cary, Ill., for a biocompatible thermoplastic elastomer), KRATON (a trademark of Shell Chemical Company of Houston, Tex., for a biocompatible thermoplastic elastomer), cellulose, C-FLEX (a trademark of Consolidated Polymer Technologies of Largo, Fla., for a biocompatible thermoplastic elastomer), polyvinylchloride and the like. The device may be of the same general thickness throughout, or it may have areas of relatively greater or lesser thickness. Alternatively, woven materials such as natural or synthetic fibers including cotton, polyester and nylon can be used to form the body of the device of the present invention.

Figure 1:
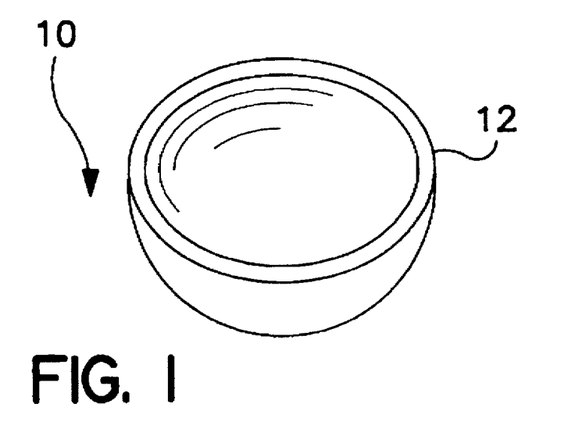
FIG. 1 is a perspective view of one embodiment of a urinary continence device of the present invention.
Figure 2:
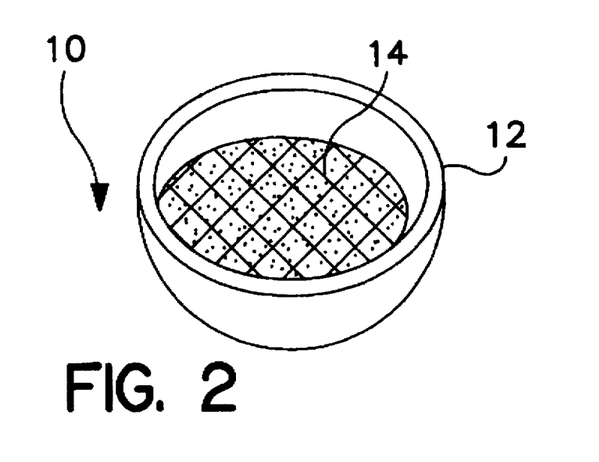
FIG. 2 is a perspective view of the preferred embodiment of a urinary continence device of the present invention.

The body is sized and shaped to conformably secure to the penis and to seal the urethra of the wearer. Generally, the body will cover the glans penis but the body may be smaller or larger, even large enough that the body extends over the shaft of the penis. FIGS. 1 and 2 show the preferred shape and size of the body of the device of the present invention, a substantially hemispherical configuration sized to fit on the glans penis. It will be recognized that the hemispherical shape may be irregular as well. Additionally, the shape of the body may vary, and certainly other configurations fall within the teachings of the present invention, some of which are described below.

With the embodiment of the device shown in FIG. 1, the material of the body 12 conformably secures the device 10 to the penis and seals the urethra of the wearer by providing a barrier at the meatus urinarius to prevent leakage of urine from the urethra. To accomplish both functions, the material making up the body 12 will be made thin, and soft and flexible enough so that the body can adapt to varying penile sizes and can conform to the shape of the penis so as to seal the urethra at the meatus urinarius. The body may form a compression fit with the penis. For example, the material of the body is elasticized, or has elasticized areas to conformably secure the body to the penis. Alternatively, the body is shaped and sized so as to perform as a suction cup, forming a vacuum fit to secure the device to the glans penis and provide a sealing of urine. The device may itself be configured as a suction cup or may be configured with an array of relatively smaller suction cups disposed about the body of the device, securing the device to the penis.

Alternatively, one or more adhesives 14 may be used to adhere the body to the penis. The adhesive may also provide some additional sealing properties if urine expels from the urethra while the device is in place. Adhesives suitable for use in the present invention include both natural and synthetic materials. Preferred adhesives include, but are not limited to, hydrogel adhesives, polyvinylether-based adhesives, hydrocolloid, acrylic-based adhesives and natural gum and synthetic rubber adhesives. Other biocompatible adhesive materials known to those skilled in the art may also be used. A removable sheet (not shown) may be provided over the adhesive to protect the adhesive until the device is to be used.

The adhesive or adhesives chosen for use in the present invention may be any adhesive that comfortably bonds to tissue and can subsequently be removed completely by mechanical force and leave no residue on the penis. Other objectives may be accomplished by selection of an appropriate adhesive. It may be important that the adhesive chosen be strong or relatively weak, depending on the intended uses and configuration of the device. If the device is intended to be used more than once, or through more than one voiding, the adhesive chosen must be capable of holding the device to the penis each time it is reapplied. Moreover, selection of an appropriate adhesive will be determined by the condition of the area to which the device will be applied, i.e., will the skin be dry or wet initially, and/or will the skin remain that way. It may be useful to have an adhesive that has a low initial tack, but whose tackiness increases in the presence of moisture. Alternatively, good initial tack may be important for the particular user of the device and/or good long term adhesion. Different adhesives may be selected for different areas of the body or more than one adhesive may be used in any one area of the body of the device. One skilled in the art will easily select the appropriate adhesive or adhesives using the teachings of the present invention.

When one or more adhesive is used, the adhesive layer may be placed in a continuous or discontinuous manner on the interior or exterior of the body 12. For uncircumcised men, it may be advantageous to place adhesive on the exterior of the body 12, and secure the device to the foreskin of the uncircumcised penis. In the following discussion, adhesive is described in use on the interior of the body, but this description is for illustration only and should not be considered to limit the invention to use of adhesive only on the interior of the body.

The at least one adhesive 14 is shown placed in a continuous layer on the interior of the body 12 in FIG. 2. In another embodiment, for example, the one or more adhesives may be situated in concentric rings throughout the interior of the body in varying arrangements. In still another embodiment, the adhesive or adhesives may be placed in any discontinuous regular or irregular arrangement on the interior of the body 12, as needed to anchor the body 12 to the penis.

Figure 11:
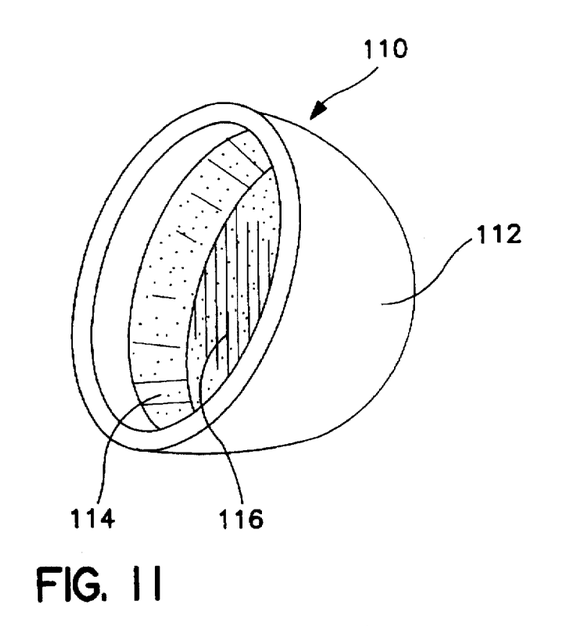
FIG. 11 is a perspective view of a further embodiment of the urinary continence device of the present invention.

FIG. 11 illustrates a device 110 according to the present invention having a body 112 in a substantially hemispherical configuration, separated into two regions, region 114 comprising a ring along the interior rim of body 112, and second region 116 including the remaining portions of the interior of the body 112. A device according to FIG. 11 may include different types of adhesives in the different regions 114, and 116 of the body of the device. The placement of an adhesive in region 114 provides optimal fixation for the device of the present invention. Second region 116 may be without adhesive so that no adhesive is present in the immediate area of the urethral opening, second region 116 may be provided with a different type of adhesive, and/or the second region 116 may be provided with a hydrophilic material that swells in the presence of moisture.

An alternative type of adhesive useful with the device of the present invention is a hydrophilic adhesive. A hydrophilic adhesive is a crosslinked polymeric material that swells or bulks when an amount of liquid touches the adhesive. When the adhesive swells, it may provide additional protection at the meatus to seal the urethra. A hydrocolloid material, for example, can have hydrophilic properties and will be useful in the present invention. Additional hydrophilic materials that can be added to or are present as constituents of adhesive materials useful in the present invention are methylcellulose, hydroxypropyl cellulose and polyvinyl acid. This hydrophilic adhesive may be used as the adhesive throughout the interior of the body, or it may be used in selected areas, for example, at that portion of the interior of the body that will be positioned proximal to the meatus. With reference to FIG. 11, use of a hydrophilic adhesive in region 116 will provide additional sealing properties for a device according to the present invention. Once moisture contacts the hydrophilic adhesive in region 116, the adhesive would swell and the swelling in that region of the body 112 will occlude the urethra at the meatus to enhance the seal of the urethra at the meatus.

FIG. 2 illustrates the preferred hemispherical configuration for the body 12 of the urinary continence device 10 of the present invention. In that figure, the body 12 is provided with a continuous layer of adhesive 14 in its interior, although a discontinuous layer of adhesive can be used with the device of the present invention, and in most cases, is preferable. When the adhesive is applied in a discontinuous layer, it is possible that the same portion of skin on the penis will not always be in contact with adhesive, a distinct advantage for those men whose skin may be irritated by the adhesive.

Figure 3:
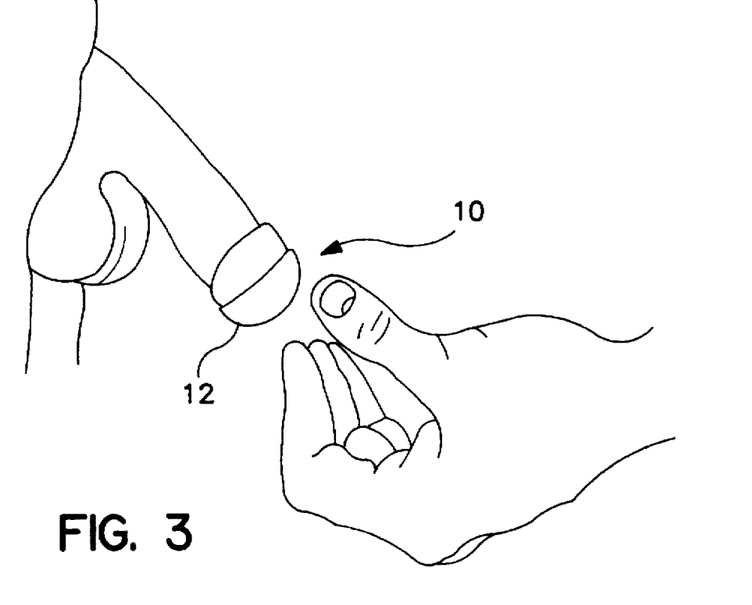
FIG. 3 illustrates the device shown in FIG. 2 in place for use.

In FIG. 3, the preferred hemispherical configuration of device 10 is shown in place on the penis. Placement of the device 10 is a simple operation and will be performed by the wearer. In general, the body 12 will be positioned proximal to the penis, and then it is moved onto the penis by the wearer. The body 12 will be fabricated so as to be conformable, so that a conformable fit is achieved with the penis and the device 10 seals the urethra at the meatus urinarius to maintain continence. If adhesive is provided on the body 12, it will serve to anchor the device 10 to the penis. Additionally, the adhesive may provide additional sealing advantages for the device of the present invention, as described above.

Figure 4:
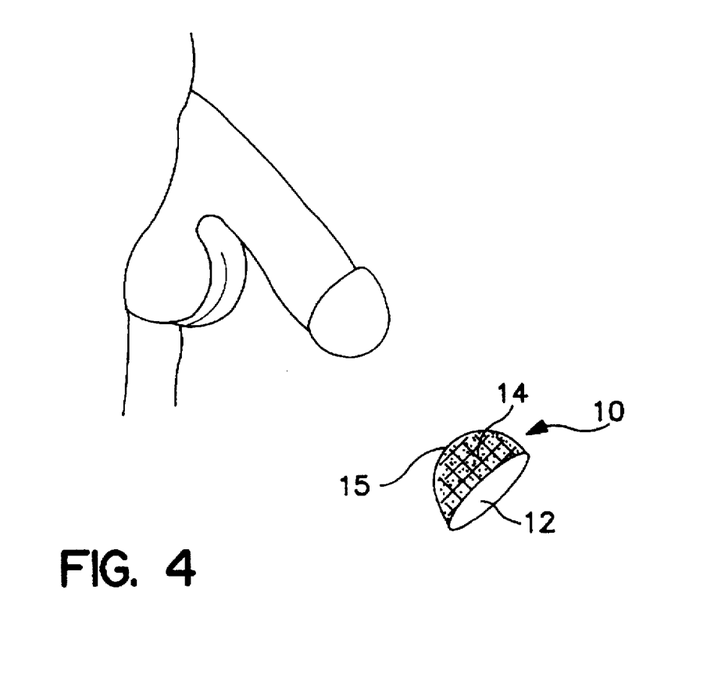
FIG. 4 illustrates the device of FIG. 2, inverted to facilitate positioning of the device for use.

Alternatively, the device 10 of the present invention can be inverted to facilitate placement of the device 10 on the wearer. As shown in FIG. 4, the body 12 is inverted so that its interior, in this instance having adhesive 14, is exposed. The top of the interior, indicated by reference number 15, is placed adjacent to the penis, and then the body 12 is rolled down over the penis to cover it and due to the nature of the material from which it is fabricated, the device 10 will conform to the shape of the penis.

Figure 5:
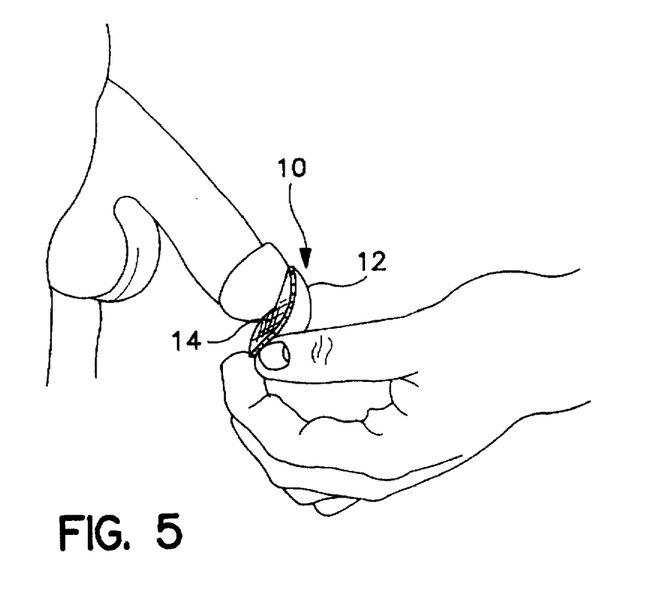
FIG. 5 illustrates a method to remove a urinary continence device of the present invention.

For removal as shown in FIG. 5, the wearer will grasp an edge of the body 12 and peel off the device 10. All traces of adhesive, if adhesive was used with the device, will be removed from the penis as well. Alternatively, the body 12 may be provided with an appendage, such as a tab 23 shown in FIGS. 6 and 7, to facilitate grasping the device for placement and/or removal.

The device of the present invention can be provided with additional means to aid in its removal. For example, a device according to the present invention can have areas on the surface of the body that are substantially thinner and therefore weaker than the remaining parts of the body. When removal of the device is desired, the wearer will grasp the device, or an appendage provided on the device, and pull. As the thinner areas are less resistant to forces applied, those areas will give way and break, in a manner similar to the manner in which perforations in paper break upon application of force, and the device, or a portion of the device, will peel away.

Figure 6:
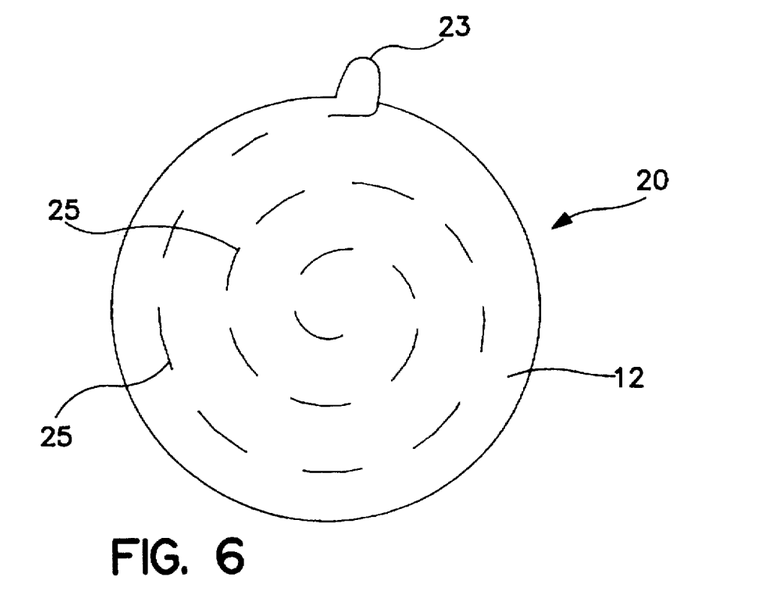
FIG. 6 is a plan frontal view of another embodiment of the urinary continence device of the present invention.
Figure 7:
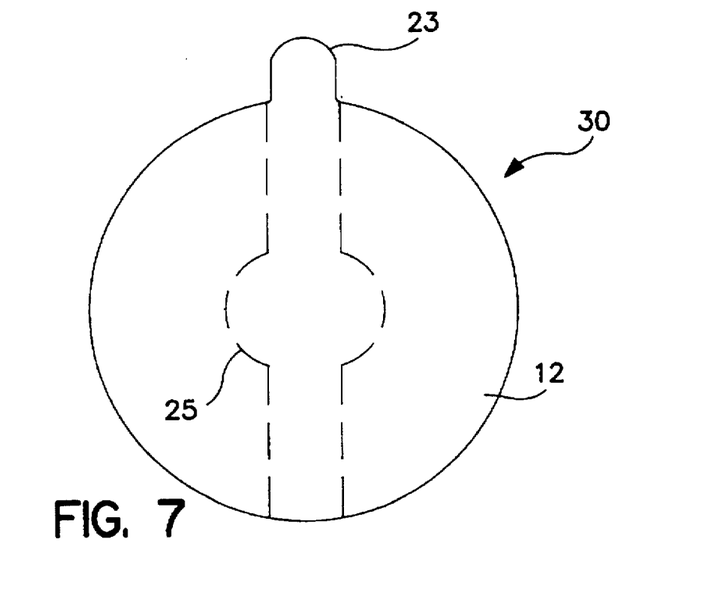
FIG. 7 is a plan frontal view of yet another embodiment of the urinary continence device of the present invention.

Two examples of this embodiment are shown with urinary continence device 20 in FIG. 6 and device 30 in FIG. 7, with reference number 25 indicating the thinner, weaker areas of the body 12. Those skilled in the art will recognize that the thinner areas 25 of the body can be positioned in other configurations as well. With the configuration shown in FIG. 7, it is not necessary to remove the device 30 completely prior to voiding. The wearer will pull on the tab 23, and peel away the region of the body bounded by the thinner areas 25 to void. The device 30 may be removed later.

Selection of appropriate adhesives will enhance the advantages of this embodiment of the present invention. For example, the device in FIG. 7 may be made reusable, with the region of the body bounded by thinner areas 25 having adhesive that will secure upon the initial application and will hold the device to the penis when it is reapplied after voiding. The regions of the body outside thinner areas 25 may be secured to the penis without adhesive as described above, or an adhesive can be selected for good long term hold.

The device of the present invention may be used for an extended period, and may be reapplied following each evacuation of the bladder. Alternatively, the wearer may choose to use a fresh device following each voiding. It can be seen that the configuration of the device of the present invention enables the device to achieve a compact form for packaging to allow one or more of the device to be carried discretely until they are to be used. For example, the device can be carried in a package having an envelope type shape, that may optionally have a lining of a substance designed to prevent deterioration of the device or the adhesive, if used, such as aluminum foil. For this type of package, the body 12 of the device is folded onto itself flat, so that the surfaces of the interior of the body (and/or the adhesive thereon) meet, and then the device can be easily carried in the package. When the device is removed from the package, the interior of the body is pulled apart so that the device retains its three dimensional shape, and the device is ready to be placed on the penis.

Figure 8:
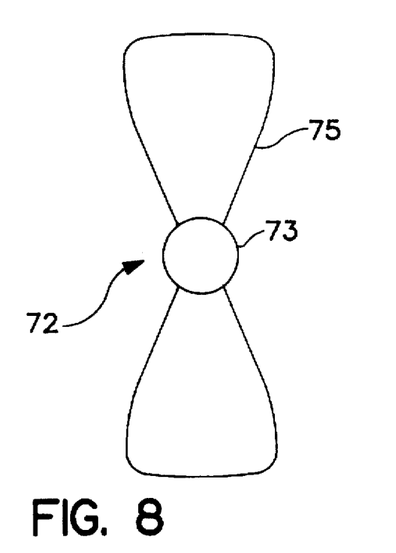
FIG. 8 is a plan frontal view of still another embodiment of the urinary continence device of the present invention.
Figure 9:
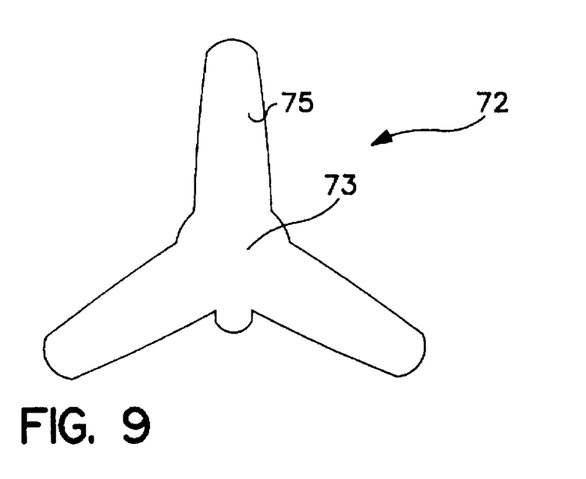
FIG. 9 is a plan frontal view of another embodiment of the urinary continence device of the present invention.
Figure 10:
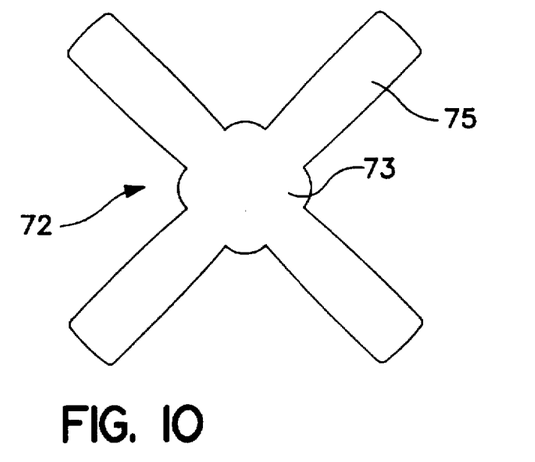
FIG. 10 is a plan frontal view of yet another embodiment of the urinary continence device of the present invention.

One skilled in the art will recognize that alternative shapes and configurations can be used for the body of the urinary continence device of the present invention. For example, the material of the body need not be continuous, as long as the geometry of the body is sufficient to allow the body to abut and seal the urethra at the meatus and to be pressingly fastenable to the penis. FIGS. 8, 9 and 10 illustrate alternative configurations for the body of the device of the present invention having a body 72 comprising an inner portion 73 configured so as to cover the meatus urinarius and two, three and four projections 75, respectively, radiating from the inner portion 73 for anchoring the device to the penis. The projections 75 can radiate from and are spaced around the inner portion 73 in a symmetrical fashion, a substantially equal distance from one another, as shown in FIGS. 8 and 9. Alternatively, the arrangement of the projections may be asymmetrical and/or the distance between the projections may be variable, as shown in FIG. 10. For a device according to this embodiment of the present invention, two or more projections, preferably up to four, is optimal.

The projections 75 may be shaped as needed to ensure that the projections can adhere to the penis and anchor the device in place. For example, the projections may have a substantially continuous width one end to the other. Alternatively, the width of the projections may become smaller or larger from one end of projection 75 resting at inner portion 73 to the other end of the projection 75 distal to the inner portion 73. The projections preferably will be sized in length so as to extend over the glans penis and to anchor the device to the penis. The projections may have adhesive on the side of each projection that will rest proximal to the penis and the adhesive may be in a continuous or discontinuous layer.

A device according to this embodiment of the present invention works in substantially the same manner as the embodiment described above. For placement, the device is placed adjacent to the penis, and is moved so that inner portion 73 covers the meatus urinarius. The two or more projections 75 are secured to the penis. Alternatively, the device can be inverted for placement, as described above. At that time the wearer wishes to remove the device, he peels the device off. This embodiment of the present invention is flat prior to placement. Accordingly, one or more of the device are easily carried, for example in the envelope type shaped package described above, for future use.

A device according to this embodiment of the present invention has an additional advantage for those men for whom the material of the device and/or the adhesive may cause skin irritation. Because not all areas of the penis are covered by the projections at all times, the wearer can orient the projections on the penis to cover different parts of the penis with subsequent wearings as necessary to prevent skin irritation. For example, with a device having two projections, during one usage, the projections can be oriented in a north-south configuration. When the device is subsequently removed and reapplied, the projections can be oriented in an east-west configuration.

Figures 12, 13:
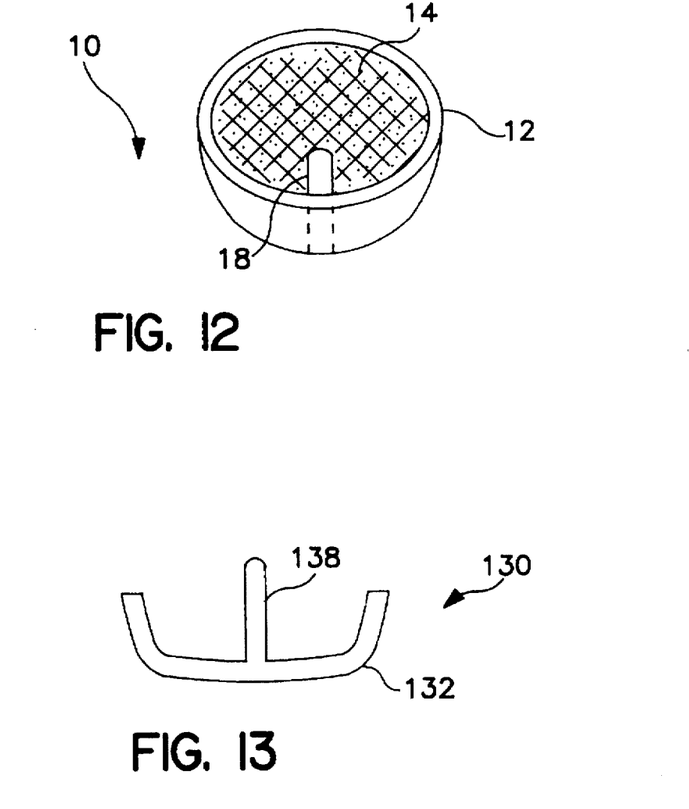
FIG. 12 is a perspective view of a urinary continence device according to the present invention having an additional locating member.
FIG. 13 is a cross sectional view of a urinary continence device according to the present invention having a locating member that provides additional sealing properties to the device.

The device of the present invention may be provided with additional members to assist the wearer in placement of the device on the penis. FIG. 12 illustrates the preferred hemispherical configuration of the urinary continence device of the present invention having an additional member to assist the wearer to place the device for use. A post 18 is provided on the interior of the body 12 at the region of the body 12 intended to cover the meatus urinarius. The post 18 will preferably be of sufficient length to rest in the urethra proximal to the meatus urinarius yet not long enough to cause any appreciable sensation to the wearer. Prior to placement of the device, the post 18 is inserted into the urethra, with the device in a normal or inverted position. After the post 18 is inserted in the urethra, the device is applied as described above. Additionally, post 18 may be coated with or made from a hydrophilic material or hydrophilic adhesive. In the presence of moisture, i.e. urine, post 18 will expand or soften to further block urine leakage. Of course, this additional member may be provided with alternative configurations of the device according to the present invention, including but not limited to, the embodiments of the device shown in the figures.

Figure 14:
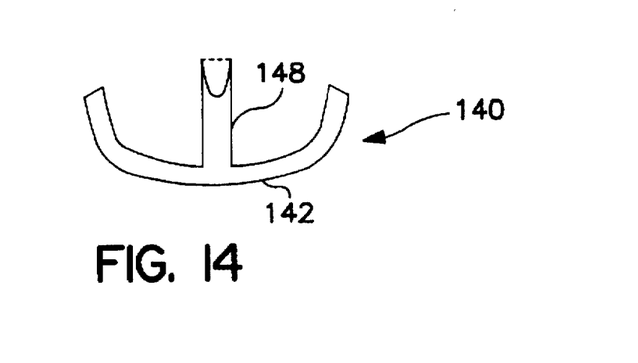
FIG. 14 is a cross sectional view of a urinary continence device according to the present invention having an alternative locating member that provides additional sealing properties to the device.

An alternative locating member, shown in FIGS. 13 and 14, provides an additional means to maintain continence with a device according to the present invention. Device 130, 140 include body 132, 142 and insertable tip 138, 148 provided on the interior of the body 132, 142 at the region of the body 132, 142 intended to cover the meatus urinarius. Insertable tip 138, 148 will be of sufficient length to extend into the urethra through the navicular fossa of urethra into the spongy part of urethra just proximal to the navicular fossa. Insertable tip 138, 148 will block the flow of urine due to its presence at that point in the urethra.

Insertable tip 138 may be semi-rigid, as shown in FIG. 13. Alternatively, as shown in FIG. 14, insertable tip 148 can be soft, deforming in the presence of urine from the shape shown in the dotted line in the figure, into, for example, the shape of a cup that will hold the urine to prevent leakage. Additionally, insertable tip 138, 148 may be coated with or made from a hydrophilic material or hydrophilic adhesive. In the presence of moisture, i.e. urine, insertable tip 138, 148 will expand or soften to further block urine leakage. Of course, the post 18 described in reference to FIG. 12 may, in fact, be a deformable post as described herein.

A device according to the present invention provides advantages over the known art, especially for those men suffering with urinary stress incontinence. The device is discrete, comfortable and effective when in use and easy for the wearer to carry and use. Little or no urine escapes from the urethra, so undesirable odors are virtually eliminated. Compared to other known treatments, the device of the present invention is substantially risk free and relatively inexpensive for long term use.

While the invention has been particularly shown and described with reference to the aforementioned embodiments, it will be understood by those skilled in the art that various changes in form, composition and detail may be made therein without departing from the spirit and scope of the invention. Any modification to the shape, configuration and/or composition of the elements comprising the invention is within the scope of the present invention.

What is claimed is:

1. A urinary continence device for men comprising:
   a body configured to cover the meatus urinarius, said body capable of providing a conformable fit with the penis and of sealing the urethra; and
   a locating member protruding inwardly from the internal surface of the body toward the penis in the region of the body that will cover the meatus urinarius when the device is in use.

2. The device of claim 1 wherein the locating member is sized so as to rest in the urethra proximal to the meatus urinarius when the device is in use.

3. The device of claim 1 wherein the locating member is sized so as to rest just beyond the navicula fossa in the spongy part of the urethra when the device is in use.

4. The device of claim 1 wherein the locating member is deformable.

5. The device of claim 1 wherein the locating member comprises a hydrophilic material.

6. The device of claim 1 wherein the locating member is coated with a hydrophilic material.

7. A urinary continence device for men comprising:
   a conformable body configured to cover the meatus urinarius, said body being capable of sealing the urethra;
   at least one adhesive positioned on the body to removably secure the body to the penis; and
   a locating member protruding inwardly from the internal surface of the body toward the penis in the region of the body that will cover the meatus urinarius when the device is in use.

8. The device of claim 7 wherein the locating member is sized so as to rest in the urethra proximal to the meatus urinarius when the device is in use.

9. The device of claim 7 wherein the locating member is sized so as to rest just beyond the navicula fossa in the spongy part of the urethra when the device is in use.

10. The device of claim 7 wherein the locating member is deformable.

11. The device of claim 7 wherein the locating member comprises a hydrophilic material.

12. The device of claim 7 wherein the locating member is coated with a hydrophilic material.

13. A method of controlling urinary incontinence in men comprising:
   providing a urinary continence device comprising a body configured to cover the meatus urinarius, said body capable of providing a conformable fit with the penis and of sealing the urethra;
   said body further comprising a locating member protruding inwardly from the internal surface of the body toward the penis in the region of the body that will cover the meatus urinarius when the device is in use;
   inverting the body;
   positioning the urinary continence device and locating member adjacent to the penis so that the body abuts the meatus urinarius and the top of the interior of the body is positioned adjacent the penis;
   placing the locating member into the urethra;
   conforming the body to the shape of the penis by reinverting the inverted device back onto the penis; and
   securing the body of the urinary continence device to the penis.

* * * * *